US010534514B2

(12) United States Patent
Gilley et al.

(10) Patent No.: US 10,534,514 B2
(45) Date of Patent: *Jan. 14, 2020

(54) VARIABLE I/O INTERFACE FOR PORTABLE MEDIA DEVICE

(71) Applicant: Apple Inc., Cupertino, CA (US)

(72) Inventors: Glenn Gregory Gilley, Los Altos, CA (US); Sarah A. Brody, Santa Clara, CA (US); Randall Hayes Ubillos, San Francisco, CA (US); Mihnea Calin Pacurariu, Los Gatos, CA (US)

(73) Assignee: APPLE INC., Cupertino, CA (US)

( * ) Notice: Subject to any disclaimer, the term of this patent is extended or adjusted under 35 U.S.C. 154(b) by 185 days.

This patent is subject to a terminal disclaimer.

(21) Appl. No.: 15/865,219

(22) Filed: Jan. 8, 2018

(65) Prior Publication Data

US 2018/0129388 A1 May 10, 2018

Related U.S. Application Data

(63) Continuation of application No. 14/274,940, filed on May 12, 2014, now Pat. No. 9,864,491, which is a
(Continued)

(51) Int. Cl.
*G06F 3/048* (2013.01)
*G06Q 10/10* (2012.01)
(Continued)

(52) U.S. Cl.
CPC ........ *G06F 3/0484* (2013.01); *A63B 24/0075* (2013.01); *G06F 1/169* (2013.01);
(Continued)

(58) Field of Classification Search
CPC .... G06F 3/0482; G06F 3/04847; G06F 1/169; G06F 1/1662; G06F 1/1626; G16H 20/30;
(Continued)

(56) References Cited

U.S. PATENT DOCUMENTS

| 3,675,640 A | 7/1972 | Gatts |
| 4,649,552 A | 3/1987 | Yukawa |

(Continued)

FOREIGN PATENT DOCUMENTS

| EP | 1462979 A1 | 9/2004 |
| EP | 1512370 B1 | 3/2005 |

(Continued)

OTHER PUBLICATIONS

"Microsoft Zune Impressions—Part 1," DigitalArts Online Magazine, Dec. 4, 2006, 6 pages.
(Continued)

*Primary Examiner* — Jordany Nunez

(74) *Attorney, Agent, or Firm* — Van Court & Aldridge LLP

(57) ABSTRACT

The present invention can include electronic devices having variable input/output interfaces that can allow a user to interact with the devices with greater efficiency and in a more ergonomic manner. An electronic device of the present invention can display icons associated with user-programmable parameters of a media file. By interacting with the icons, a user can change the user-programmable parameters during playback of the media file. Changes to the user-programmable parameters can affect playback of the remainder of the media file. An electronic device of the present invention also can automatically re-orient images shown on a display and re-configure user input components based on the orientation of the electronic device.

20 Claims, 13 Drawing Sheets

Related U.S. Application Data continuation of application No. 11/729,291, filed on Mar. 27, 2007, now Pat. No. 8,745,496.

(60) Provisional application No. 60/846,414, filed on Sep. 21, 2006.

(51) Int. Cl.

| | |
|---|---|
| *A63B 21/06* | (2006.01) |
| *G06F 3/0484* | (2013.01) |
| *G06F 1/16* | (2006.01) |
| *G06F 3/0482* | (2013.01) |
| *A63B 24/00* | (2006.01) |
| *G06F 19/00* | (2018.01) |
| *G16H 20/30* | (2018.01) |
| *G16H 10/65* | (2018.01) |

(52) U.S. Cl.
CPC .......... *G06F 1/1626* (2013.01); *G06F 1/1643* (2013.01); *G06F 1/1662* (2013.01); *G06F 3/0482* (2013.01); *G06F 3/04847* (2013.01); *G06F 19/3481* (2013.01); *G16H 10/65* (2018.01); *G16H 20/30* (2018.01); *A63B 24/0062* (2013.01); *A63B 2225/20* (2013.01); *A63B 2225/50* (2013.01); *G06F 2200/1614* (2013.01); *G06F 2200/1637* (2013.01)

(58) Field of Classification Search
CPC ............ A63B 24/0075; A63B 2225/20; A63B 24/0062
See application file for complete search history.

(56) References Cited

U.S. PATENT DOCUMENTS

| | | | |
|---|---|---|---|
| 4,907,795 | A | 3/1990 | Shaw et al. |
| 5,379,057 | A | 1/1995 | Clough et al. |
| 5,412,564 | A | 5/1995 | Ecer |
| 5,434,913 | A | 7/1995 | Tung et al. |
| 5,452,435 | A | 9/1995 | Malouf et al. |
| 5,471,405 | A | 11/1995 | Marsh |
| 5,489,249 | A | 2/1996 | Brewer et al. |
| 5,490,247 | A | 2/1996 | Tung et al. |
| 5,645,509 | A | 7/1997 | Brewer et al. |
| 5,673,691 | A | 10/1997 | Abrams et al. |
| 5,675,362 | A | 10/1997 | Clough et al. |
| 5,794,018 | A | 8/1998 | Vrvilo et al. |
| 5,819,735 | A | 10/1998 | Mansfield et al. |
| 5,857,939 | A | 1/1999 | Kaufman |
| 5,859,979 | A | 1/1999 | Tung et al. |
| 5,890,995 | A | 4/1999 | Bobick et al. |
| 5,890,997 | A | 4/1999 | Roth |
| 5,913,062 | A | 6/1999 | Vrvilo et al. |
| 5,954,640 | A | 9/1999 | Szabo |
| 5,976,083 | A | 11/1999 | Richardson et al. |
| 6,013,007 | A | 1/2000 | Root et al. |
| 6,032,108 | A | 2/2000 | Seiple et al. |
| 6,039,688 | A | 3/2000 | Douglas et al. |
| 6,077,193 | A | 6/2000 | Buhler et al. |
| 6,135,951 | A | 10/2000 | Richardson et al. |
| 6,159,131 | A | 12/2000 | Pfeffer |
| 6,357,147 | B1 | 3/2002 | Darley et al. |
| 6,447,424 | B1 | 9/2002 | Ashby et al. |
| 6,463,385 | B1 | 10/2002 | Fry |
| 6,527,674 | B1 | 3/2003 | Clem |
| 6,539,336 | B1 | 3/2003 | Vock et al. |
| 6,553,037 | B1 | 4/2003 | Pivowar et al. |
| 6,560,903 | B1 | 5/2003 | Darley |
| 6,582,342 | B2 | 6/2003 | Kaufman |
| 6,585,622 | B1 | 7/2003 | Shum et al. |
| 6,587,127 | B1 | 7/2003 | Leeke et al. |
| 6,619,835 | B2 | 9/2003 | Kita |
| 6,623,427 | B2 | 9/2003 | Mandigo |
| 6,702,719 | B1 | 3/2004 | Brown et al. |
| 6,716,139 | B1 | 4/2004 | Hosseinzadeh-Dolkhani et al. |
| 6,725,281 | B1 | 4/2004 | Zintel et al. |
| 6,735,568 | B1 | 5/2004 | Buckwalter et al. |
| 6,749,537 | B1 | 6/2004 | Hickman |
| 6,790,178 | B1 | 9/2004 | Mault et al. |
| 6,793,607 | B2 | 9/2004 | Neil |
| 6,808,473 | B2 | 10/2004 | Hisano et al. |
| 6,898,550 | B1 | 5/2005 | Blackadar et al. |
| 6,910,068 | B2 | 6/2005 | Zintel et al. |
| 6,921,351 | B1 | 7/2005 | Hickman et al. |
| 6,945,911 | B2 | 9/2005 | Jackowski |
| 7,030,735 | B2 | 4/2006 | Chen |
| 7,062,225 | B2 | 6/2006 | White |
| 7,069,308 | B2 | 6/2006 | Abrams |
| 7,070,539 | B2 | 7/2006 | Brown et al. |
| 7,085,590 | B2 | 8/2006 | Kennedy et al. |
| 7,158,844 | B1 * | 1/2007 | Cancilla .................. H04S 7/40 381/303 |
| 7,171,331 | B2 | 1/2007 | Vock et al. |
| 7,174,227 | B2 | 2/2007 | Kobayashi et al. |
| 7,192,387 | B2 | 3/2007 | Mendel |
| 7,200,517 | B2 | 4/2007 | Darley et al. |
| 7,228,168 | B2 | 6/2007 | Dardik et al. |
| 7,251,454 | B2 | 7/2007 | White |
| 7,254,516 | B2 | 8/2007 | Case, Jr. et al. |
| 7,261,690 | B2 | 8/2007 | Teller et al. |
| 7,277,726 | B2 | 10/2007 | Ahya et al. |
| 7,278,966 | B2 | 10/2007 | Hjelt et al. |
| 7,292,867 | B2 | 11/2007 | Werner et al. |
| 7,328,239 | B1 | 2/2008 | Berberian et al. |
| 7,353,139 | B1 | 4/2008 | Burrell et al. |
| 7,424,718 | B2 | 9/2008 | Dutton |
| 7,454,002 | B1 | 11/2008 | Gardner et al. |
| 7,496,277 | B2 | 2/2009 | Ackley et al. |
| 7,519,327 | B2 | 4/2009 | White |
| 7,523,040 | B2 | 4/2009 | Kirchhoff et al. |
| 7,526,524 | B2 | 4/2009 | White |
| 7,591,760 | B2 | 9/2009 | Gordon et al. |
| 7,603,255 | B2 | 10/2009 | Case, Jr. et al. |
| 7,618,345 | B2 | 11/2009 | Corbalis et al. |
| 7,628,730 | B1 | 12/2009 | Watterson et al. |
| 7,636,754 | B2 | 12/2009 | Zhu et al. |
| 7,656,824 | B2 | 2/2010 | Wang et al. |
| 7,670,263 | B2 | 3/2010 | Ellis et al. |
| 7,683,252 | B2 | 3/2010 | Oliver et al. |
| 7,753,825 | B2 | 7/2010 | Jaquish et al. |
| 7,765,245 | B2 | 7/2010 | Nichols et al. |
| 7,827,039 | B2 | 11/2010 | Butcher et al. |
| 7,841,967 | B1 | 11/2010 | Kahn et al. |
| 7,946,959 | B2 | 5/2011 | Shum et al. |
| 7,973,231 | B2 | 7/2011 | Bowen |
| 8,001,472 | B2 | 8/2011 | Gilley et al. |
| 8,066,514 | B2 | 11/2011 | Clarke |
| 8,095,120 | B1 | 1/2012 | Blair et al. |
| 8,311,656 | B2 * | 11/2012 | Carrier ................ G10H 1/0008 700/94 |
| 8,529,409 | B1 | 9/2013 | Lesea-Ames |
| 8,930,204 | B1 | 1/2015 | Igoe et al. |
| 2001/0054180 | A1 | 12/2001 | Atkinson |
| 2002/0007313 | A1 | 1/2002 | Mai et al. |
| 2002/0022551 | A1 | 2/2002 | Watterson et al. |
| 2002/0022774 | A1 | 2/2002 | Karnieli |
| 2002/0027164 | A1 | 3/2002 | Mault et al. |
| 2002/0033753 | A1 | 3/2002 | Imbo |
| 2002/0072932 | A1 | 6/2002 | Swamy |
| 2002/0077784 | A1 | 6/2002 | Vock et al. |
| 2002/0095460 | A1 | 7/2002 | Benson |
| 2002/0107824 | A1 | 8/2002 | Ahmed |
| 2003/0017914 | A1 | 1/2003 | Jackowski |
| 2003/0028116 | A1 | 2/2003 | Birnbaum |
| 2003/0059747 | A1 | 3/2003 | Yoshida et al. |
| 2003/0097878 | A1 | 5/2003 | Farringdon et al. |
| 2003/0175666 | A1 | 9/2003 | Tanabe et al. |
| 2003/0204412 | A1 | 10/2003 | Brier |
| 2003/0208113 | A1 | 11/2003 | Mault et al. |
| 2003/0220971 | A1 | 11/2003 | Kressin |
| 2003/0224337 | A1 | 12/2003 | Shum et al. |
| 2003/0229900 | A1 | 12/2003 | Reisman |
| 2004/0002041 | A1 | 1/2004 | Peplinski et al. |

(56) References Cited

U.S. PATENT DOCUMENTS

| | | |
|---|---|---|
| 2004/0029684 A1 | 2/2004 | Zarif |
| 2004/0091843 A1 | 5/2004 | Albro et al. |
| 2004/0102931 A1 | 5/2004 | Ellis et al. |
| 2004/0106449 A1 | 6/2004 | Walker et al. |
| 2004/0107116 A1 | 6/2004 | Brown |
| 2004/0143673 A1 | 7/2004 | Kristjansson |
| 2004/0198555 A1 | 10/2004 | Anderson et al. |
| 2004/0201595 A1 | 10/2004 | Manchester |
| 2004/0220017 A1 | 11/2004 | Gordon et al. |
| 2004/0229729 A1 | 11/2004 | Albert et al. |
| 2005/0008993 A1 | 1/2005 | Bergh et al. |
| 2005/0008994 A1 | 1/2005 | Bisogno |
| 2005/0010638 A1 | 1/2005 | Richardson et al. |
| 2005/0014113 A1 | 1/2005 | Fleck et al. |
| 2005/0034078 A1 | 2/2005 | Abbott et al. |
| 2005/0042582 A1 | 2/2005 | Graves |
| 2005/0044503 A1 | 2/2005 | Richardson et al. |
| 2005/0050464 A1 | 3/2005 | Vasey |
| 2005/0058970 A1 | 3/2005 | Perlman et al. |
| 2005/0060368 A1 | 3/2005 | Wang et al. |
| 2005/0065950 A1 | 3/2005 | Chaganti et al. |
| 2005/0070809 A1 | 3/2005 | Acres |
| 2005/0101314 A1 | 5/2005 | Levi |
| 2005/0107116 A1 | 5/2005 | Yamaguchi |
| 2005/0107216 A1 | 5/2005 | Lee et al. |
| 2005/0113649 A1 | 5/2005 | Bergantino |
| 2005/0125221 A1 | 6/2005 | Brown et al. |
| 2005/0125222 A1 | 6/2005 | Brown et al. |
| 2005/0125302 A1 | 6/2005 | Brown et al. |
| 2005/0164833 A1 | 7/2005 | Florio |
| 2005/0172311 A1 | 8/2005 | Hjelt et al. |
| 2005/0176461 A1 | 8/2005 | Bozzone et al. |
| 2005/0180341 A1 | 8/2005 | Nelson et al. |
| 2005/0202934 A1 | 9/2005 | Olrik et al. |
| 2005/0209050 A1 | 9/2005 | Bartels |
| 2005/0226172 A1 | 10/2005 | Richardson et al. |
| 2005/0227811 A1 | 10/2005 | Shum et al. |
| 2005/0240705 A1 | 10/2005 | Novotney et al. |
| 2005/0266385 A1 | 12/2005 | Bisogno |
| 2005/0287499 A1 | 12/2005 | Yeager |
| 2006/0004680 A1 | 1/2006 | Robarts et al. |
| 2006/0004862 A1 | 1/2006 | Fisher et al. |
| 2006/0025282 A1 | 2/2006 | Redmann |
| 2006/0026052 A1 | 2/2006 | Klett et al. |
| 2006/0035200 A1 | 2/2006 | Pittman |
| 2006/0040244 A1 | 2/2006 | Kain |
| 2006/0047208 A1 | 3/2006 | Yoon |
| 2006/0063980 A1 | 3/2006 | Hwang et al. |
| 2006/0085272 A1 | 4/2006 | Case et al. |
| 2006/0107822 A1 | 5/2006 | Bowen |
| 2006/0160639 A1 | 7/2006 | Klein |
| 2006/0173972 A1 | 8/2006 | Jung et al. |
| 2006/0197670 A1 | 9/2006 | Breibart |
| 2006/0197753 A1 | 9/2006 | Hotelling |
| 2006/0199155 A1 | 9/2006 | Mosher |
| 2006/0205564 A1 | 9/2006 | Peterson |
| 2006/0238517 A1 | 10/2006 | King et al. |
| 2006/0250524 A1 | 11/2006 | Roche |
| 2006/0253874 A1 | 11/2006 | Stark et al. |
| 2006/0256130 A1 | 11/2006 | Gonzalez |
| 2006/0263750 A1 | 11/2006 | Gordon |
| 2007/0026999 A1 | 2/2007 | Merolle et al. |
| 2007/0032345 A1 | 2/2007 | Padmanabhan et al. |
| 2007/0033068 A1 | 2/2007 | Rao et al. |
| 2007/0033069 A1 | 2/2007 | Rao et al. |
| 2007/0059672 A1 | 3/2007 | Shaw |
| 2007/0074618 A1* | 4/2007 | Vergo .............. G10H 1/00 84/612 |
| 2007/0074619 A1 | 4/2007 | Vergo |
| 2007/0087686 A1 | 4/2007 | Holm et al. |
| 2007/0100595 A1 | 5/2007 | Earles et al. |
| 2007/0110074 A1 | 5/2007 | Bradley et al. |
| 2007/0113726 A1 | 5/2007 | Oliver et al. |
| 2007/0130476 A1 | 6/2007 | Mohanty |
| 2007/0135264 A1 | 6/2007 | Rosenberg |
| 2007/0136093 A1 | 6/2007 | Rankin et al. |
| 2007/0141540 A1 | 6/2007 | Borg |
| 2007/0166683 A1 | 7/2007 | Chang et al. |
| 2007/0192106 A1 | 8/2007 | Zilca |
| 2007/0219059 A1 | 9/2007 | Schwartz et al. |
| 2007/0265138 A1 | 11/2007 | Ashby |
| 2007/0287596 A1 | 12/2007 | Case et al. |
| 2007/0287597 A1 | 12/2007 | Cameron |
| 2008/0033827 A1 | 2/2008 | Kuang et al. |
| 2008/0096726 A1 | 4/2008 | Riley et al. |
| 2008/0155470 A1 | 6/2008 | Khedouri et al. |
| 2008/0177860 A1 | 7/2008 | Khedouri et al. |
| 2008/0195594 A1 | 8/2008 | Gerjets et al. |
| 2008/0195997 A1 | 8/2008 | Herberger et al. |
| 2008/0215968 A1 | 9/2008 | Bekerman |
| 2008/0242521 A1 | 10/2008 | Einav |
| 2009/0047645 A1 | 2/2009 | Dibenedetto et al. |
| 2009/0087819 A1 | 4/2009 | Adachi et al. |
| 2009/0144080 A1 | 6/2009 | Gray et al. |
| 2009/0169171 A1 | 7/2009 | Massey et al. |
| 2009/0312105 A1 | 12/2009 | Koplar |
| 2009/0327894 A1 | 12/2009 | Rakib et al. |
| 2010/0081116 A1 | 4/2010 | Barasch et al. |
| 2011/0145743 A1* | 6/2011 | Brinkmann ......... G06F 3/04847 715/765 |
| 2012/0185905 A1 | 7/2012 | Kelley |
| 2012/0198317 A1 | 8/2012 | Eppolito et al. |
| 2012/0230510 A1 | 9/2012 | Dinescu et al. |
| 2013/0024880 A1 | 1/2013 | Moloney-Egnatios et al. |
| 2014/0122601 A1 | 5/2014 | Poston et al. |
| 2014/0285312 A1 | 9/2014 | Laaksonen et al. |
| 2014/0328571 A1 | 11/2014 | Roberts, Jr. et al. |
| 2014/0344045 A1 | 11/2014 | Shum et al. |
| 2015/0086174 A1 | 3/2015 | Abecassis et al. |
| 2015/0341410 A1 | 11/2015 | Schrempp et al. |

FOREIGN PATENT DOCUMENTS

| | | |
|---|---|---|
| EP | 1585014 A2 | 10/2005 |
| GB | 2253706 B | 9/1992 |
| GB | 2284060 A | 5/1995 |
| GB | 2409040 A | 6/2005 |
| JP | 2007013228 A | 1/2007 |
| KR | 19990073234 A | 10/1999 |
| WO | 9714357 | 4/1997 |
| WO | 0052604 | 9/2000 |
| WO | 0116855 | 3/2001 |
| WO | 0165460 | 9/2001 |
| WO | 0215986 | 2/2002 |
| WO | 02062425 | 8/2002 |
| WO | 02093272 | 11/2002 |
| WO | 2005032363 | 4/2005 |
| WO | 2005036918 A1 | 4/2005 |
| WO | 2005082472 A1 | 9/2005 |
| WO | 2005093633 A2 | 10/2005 |
| WO | 2005087323 A3 | 3/2006 |
| WO | 2006042415 A1 | 4/2006 |
| WO | 2006079942 | 8/2006 |
| WO | 2007099206 A1 | 9/2007 |

OTHER PUBLICATIONS

"Notice from the European Patent Office dated Oct. 1, 2007 concerning business methods." Official Journal of the European Patent Office, vol. 30, No. 7, Nov. 1, 2007, 2 pages.

"Statement in Accordance With the Notice From the European Patent Office Dated Oct. 1, 2007 Concerning Business Methods." Official Journal of the European Patent Office, Nov. 1, 2007, 1 page.

"Podfitness Delivers on myMedia Promise," Utah Tech Jobs.com, Nov. 13, 2006, 4 pages.

Creative NOMAD® Digital Audio Player User Guide, Jun. 1999. Title page (1 page), publication information page (1 page), software license agreement (2 pages), table of contents (2 pages), introduction pages (2 pages), and pp. 1-34.

Creative NOMAD® II Getting Started Guide, Jan. 2000. Title page (1 page), publication information page (1 page), software license

(56) References Cited

OTHER PUBLICATIONS agreement (2 pages), safety information (1 page), table of contents (2 pages), introduction (2 pages), and pp. 1-38.
Ericsson Inc. "Cellular Phone With Integrated MP3 Player." Research Disclosure Journal No. 41815, Research Disclosure Database No. 418015 (Feb. 1999), 2 pages.
Menta. "1200 Song MP3 Portable is a Milestone Player." http://www.mp3newswire.nel.stories/personaljuke.html. Jan. 11, 2000.4 pages.
Oliver et al. "Enhancing Exercise Performance through Real-time Physiological Monitoring and Music: A User Study." Pervasive Health Conference and Workshops, pp. 1-10 (2007).
Pike, Weight Watchers On-the-Go, Apr. 12, 2005, PC Magazine, vol. 24, Iss.6; p. 149.
Reinventing the Scroll Wheel, CNET news.com, Aug. 22, 2006, 16 pages: <http://www.news.com/2300-1041_3-6107951-1.html?tag=ne.gall.pg; http://www.news.com/2300-1041_3-6107951-2.html?tag=ne.gall.pghttp://www.news.com/2300-1041_3-6107951-3.html?tag=ne.gall.pghttp://www.news.com/2300-1041_3-6107951-4.html?tag=ne.gall.pg.
Rio 500 Getting Started Guide, 1999. 2 pages.
Rio PMP300 User's Guide (1998). Title page (1 page), copyright notices (1 page), table of contents (2 pages), and pp. 1-24).
Sensei.com, Feb. 10, 2008, 1 page.
Wallace et al. "Twelve month adherence of adults who joined a fitness program with a spouse vs without spouse." The Journal of Sports Medicine and Physical Fitness; Sep. 1995, vol. 35, No. (3), pp. 206-213.

\* cited by examiner

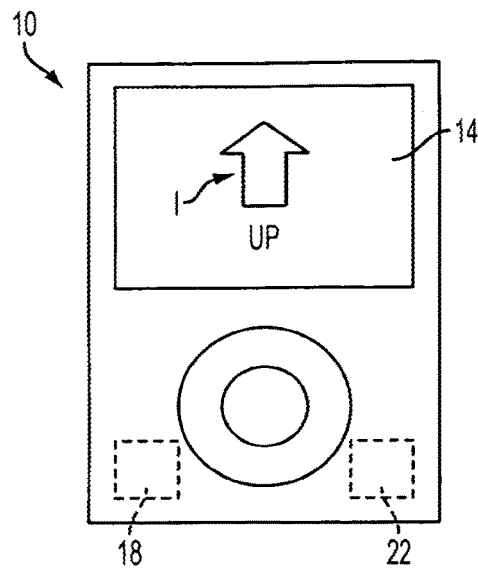
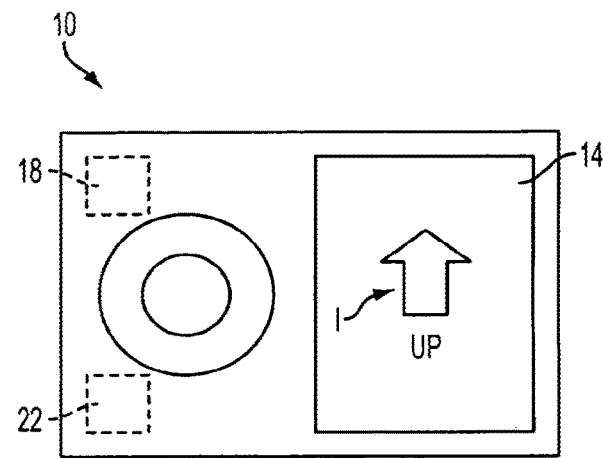
FIG. 5A    FIG. 5B
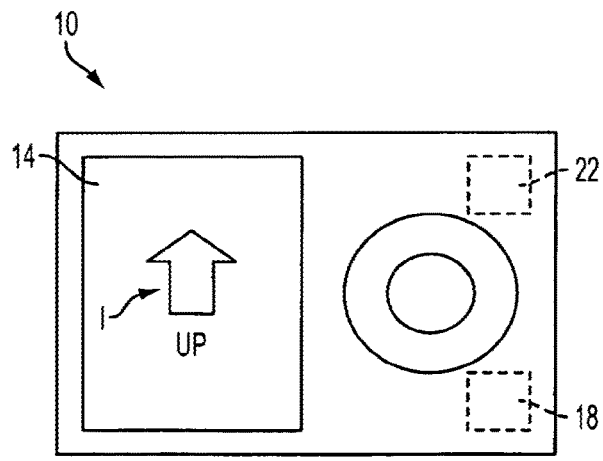
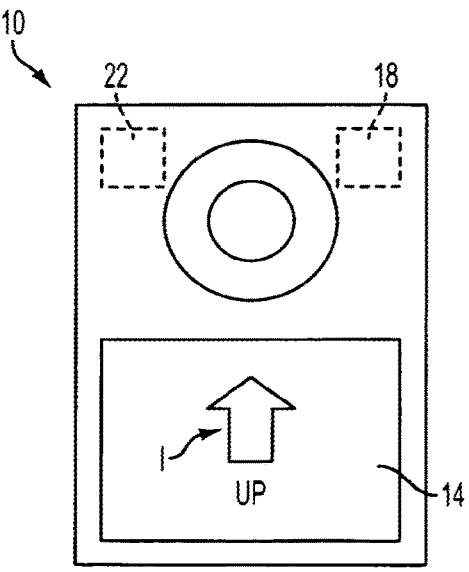
FIG. 5C    FIG. 5D
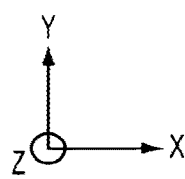

VARIABLE I/O INTERFACE FOR PORTABLE MEDIA DEVICE

CROSS-REFERENCE TO RELATED APPLICATIONS

This application is a continuation of U.S. patent application Ser. No. 14/274,940, filed on May 12, 2014 (now U.S. Pat. No. 9,864,491), which is a continuation of U.S. patent application Ser. No. 11/729,291, filed on Mar. 27, 2007 (now U.S. Pat. No. 8,745,496), which claims priority to U.S. Provisional Patent Application No. 60/846,414, filed on Sep. 21, 2006 (referred to below as "the incorporated provisional patent application"). These earlier application are incorporated herein by reference.

This also is related to:

U.S. Pat. No. 8,956,290, entitled "LIFESTYLE COMPANION SYSTEM," (referred to herein as "the incorporated LIFESTYLE COMPANION document"), the entirety of which is incorporated herein by reference;

U.S. Pat. No. 8,001,472, entitled "SYSTEMS AND METHODS FOR PROVIDING AUDIO AND VISUAL CUES VIA A PORTABLE ELECTRONIC DEVICE," (referred to herein as "the incorporated AUDIO AND VISUAL CUES document"), the entirety of which is incorporated herein by reference;

U.S. Pat. No. 8,235,724, entitled "DYNAMICALLY ADAPTIVE SCHEDULING SYSTEM,"(referred to herein as "the incorporated ADAPTIVE SCHEDULING SYSTEM document"), the entirety of which is incorporated herein by reference;

U.S. Pat. No. 8,429,223, entitled "SYSTEMS AND METHODS FOR FACILITATING GROUP ACTIVITIES," (referred to herein as "the incorporated GROUP ACTIVITIES document"), the entirety of which is incorporated herein by reference;

U.S. Publication No. 2008/0077489, entitled "REWARDS SYSTEMS," (referred to herein as "the incorporated REWARDS SYSTEMS document"), the entirety of which is incorporated herein by reference;

U.S. Publication No. 2008/0076972, entitled "INTEGRATED SENSORS FOR TRACKING PERFORMANCE METRICS," (referred to herein as "the incorporated INTEGRATED SENSORS document"), the entirety of which is incorporated herein by reference; and U.S. patent application Ser. No. 11/426,078, to King et al., filed on Jun. 23, 2006 (Publication No. 2006/0238517, published on Oct. 26, 2006), entitled "Electronic Device Having Display and Surrounding Touch Sensitive Bezel for User Interface and Control" (referred to herein as "the incorporated King document"), the entirety of which is incorporated herein by reference.

The incorporated provisional patent application, LIFESTYLE COMPANION document, AUDIO AND VISUAL CUES document, ADAPTIVE SCHEDULING SYSTEM document, GROUP ACTIVITIES document, REWARDS SYSTEMS document, INTEGRATED SENSORS document, and King document collectively are referred to herein as "the incorporated patent documents."

FIELD OF THE INVENTION

The present invention can relate to variable input/output interfaces for electronic devices.

BACKGROUND OF THE INVENTION

Currently available portable media devices may provide limited ways by which users can interact with the devices. For example, currently available portable media devices may show images on its display in only one orientation with respect to the housing of the media device. When a user places the portable media device in a non-standard orientation, the user may have to angle his head in order to properly view the displayed images. Furthermore, when the media device is playing a media file, the media device may not permit the user to adjust parameters associated with the media file. In order to adjust any of the parameters of the media file, the media device may require the user first to stop playback of the media file.

SUMMARY OF THE INVENTION

The present invention can include electronic devices that have variable input/output (I/O) interfaces. The variable I/O interfaces can allow a user to interact with the devices in a more ergonomic manner and with greater efficiency.

An electronic device of the present invention can display one or more software icons associated with user-programmable parameters of a media file during playback of the media file. The electronic device can permit a user to select a user-programmable parameter of the media file by selecting a corresponding icon. While the selected icon is visually distinguished, the electronic device can permit the user to adjust the selected user-programmable parameter. The electronic device can change the software icons it displays to reflect different user-programmable parameters associated with different modules of the media file or with different media files.

An electronic device of the present invention also can automatically re-orient an image shown on its display and/or re-configure user input components based on the orientation of the electronic device. The user input components can include hardware or software input components.

BRIEF DESCRIPTION OF THE DRAWINGS

The above and other advantages of the present invention will be apparent upon consideration of the following detailed description, taken in conjunction with accompanying drawings, in which like reference characters refer to like parts throughout, and in which:

FIGS. 5A-5I illustrate electronic devices that can automatically re-orient an image shown on its display based on the orientation of the device in accordance with one embodiment of the present invention;

DETAILED DESCRIPTION OF THE INVENTION

Figure 1:
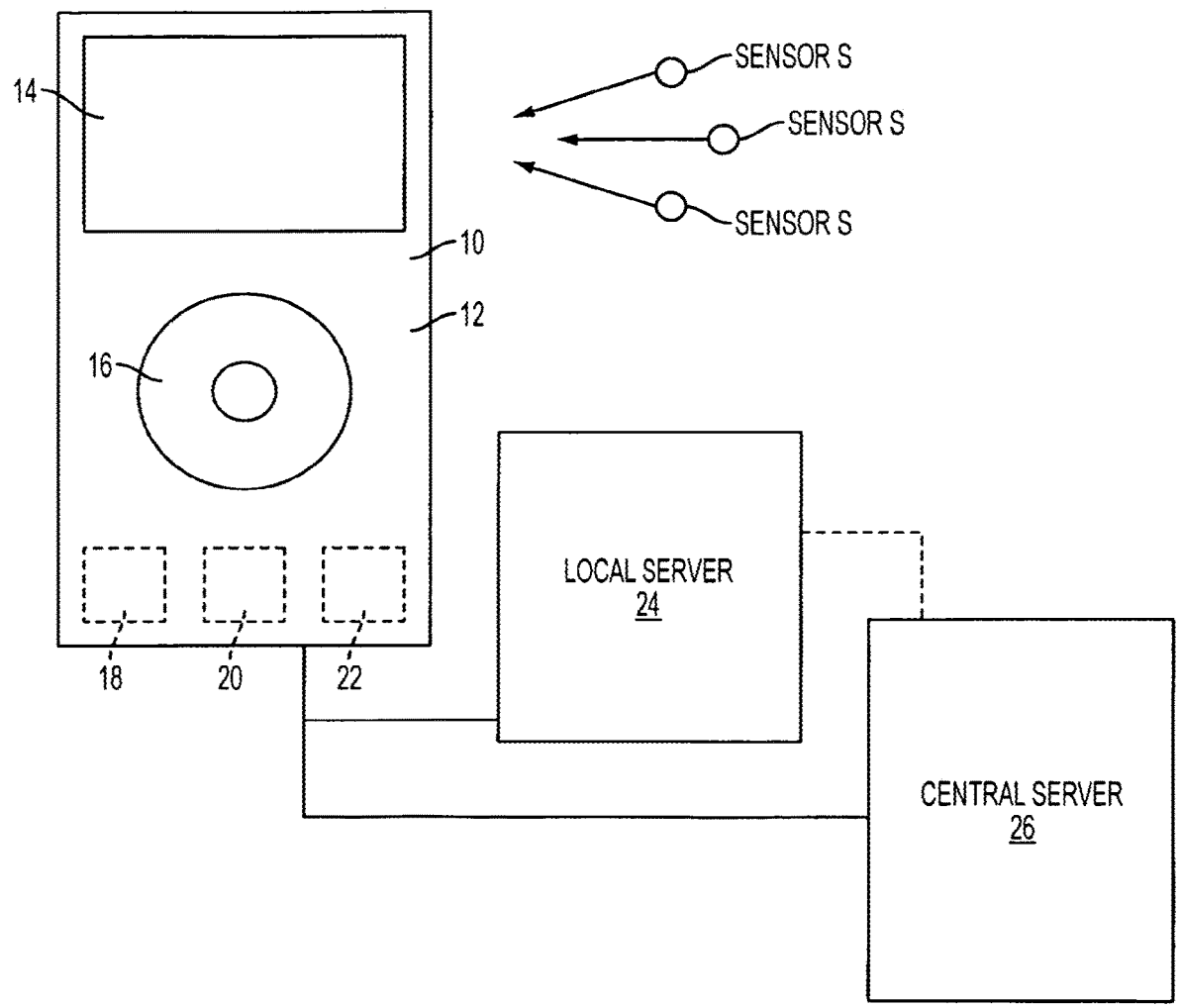
FIG. 1 illustrates one embodiment of an electronic device of the present invention in communication with a network of servers.

FIG. 1 illustrates one embodiment of an electronic device of the present invention in communication with a network of servers. Electronic device 10 can include housing 12, display 14, user input component 16, controller 18, memory 20, and orientation transducer 22. In one embodiment of the present invention, electronic device 10 can be a portable media device similar to that sold under the trademark iPod™ by Apple Computer, Inc. of Cupertino, Calif.

User input component 16 can include a clickwheel similar to that incorporated in the iPod™. The clickwheel can include one or more buttons and a touchpad. The touchpad may permit a user to scroll by running the user's finger around the track of the clickwheel. In alternative embodiments, user input component 16 can include, for example, one or more buttons, a touchpad, a touchscreen display, electronics for accepting voice commands, antennas for accepting signals from other electronic devices, infrared ports for accepting signals from other electronic devices, or any combination thereof. Controller 18 can include one or more processors, ASICs, circuits, or any combination thereof. Memory 20 can include read only memory, random access memory, solid-state memory, buffer memory, hard drive memory, any other memory known in the art or otherwise, or any combination thereof.

In accordance with one aspect of the present invention, a user can use portable media device 10, local server 24 (e.g., a user's personal computer), or central server 26 (e.g., a server that hosts a website) to design or compile a program of activities for the user to perform or for another user to perform. The program of activities can include instructions and other audio and/or visual information. The instructions and other audio/visual information can be stored in a media file, which the user can play back on, e.g., electronic device 10. For example, the incorporated patent documents describe in greater detail programs of activities (e.g., compilations of fitness activities, nutritional activities, and/or medical activities) that a user can compile, e.g., on a local or central server and playback on electronic device 10.

If the user compiles the program of activities on local server 24 or central server 26, the local or central server can transmit the media file to portable media device 10 using a cable or a wireless communication protocol known in the art or otherwise. The portable media device can store the media file in memory 20. When the user wishes to perform activities in accordance with the compiled program, controller 18 can play back the media file. Electronic device 10 can output audio data stored in the media file using speakers (not shown) disposed within portable media device 10 or an accessory coupled thereto. Portable media device 10 can output visual data stored in the media file using display 14. Visual data can include text images, still images, and/or video images.

In one aspect of the present invention, portable electronic device 10 can accept data from sensors S that can capture information about the user's activities. Sensors S can include sensors used in, for example, pedometers, accelerometers, heart rate monitors, oximeters, GPS tracking devices, devices that measure temperature, devices that measure heat flux, electrocardiogram devices, devices having activity tracking sensors similar to those described in the incorporated INTEGRATED SENSORS document, devices having activity tracking sensors similar to those described in the other incorporated patent documents, or any combination thereof.

A user can wear sensors S in the user's clothing or accessories. Alternatively, sensors S can be disposed within electronic device 10 or another electronic device utilized by the user. While the user is performing the activities programmed into the media file, sensors S can track the user's performance and electronic device 10 can log data from sensors S in memory 20. Once the user has completed the scheduled activities, the user can upload the data that electronic device 10 has collected about the user's performance into local server 24 and/or central server 26. Local server 24 and/or central server 26 then can analyze that data to adapt the user's goals or otherwise track a user's progress, for example, in ways similar to those described in the incorporated patent documents.

Figure 2A:
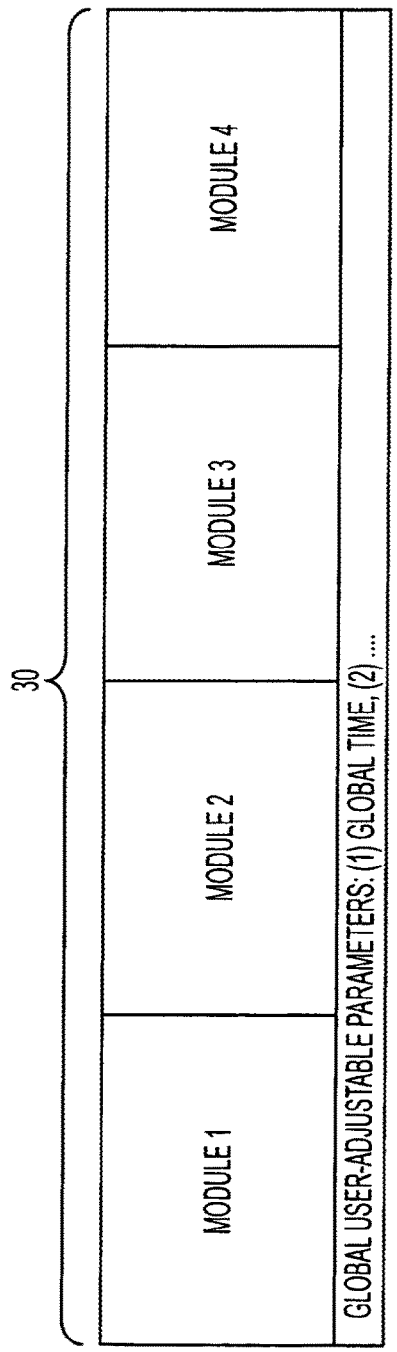
FIGS. 2A-2B illustrate a media file in accordance with one embodiment of the present invention.
Figure 2B:
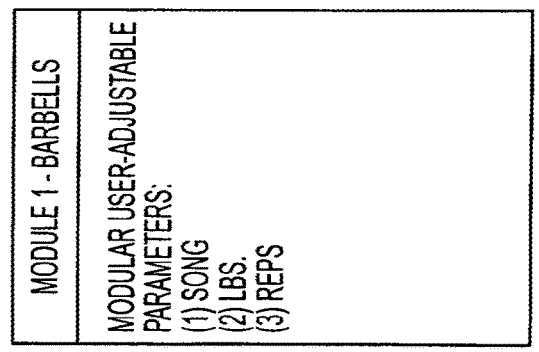

FIGS. 2A-2B illustrate a media file in accordance with one embodiment of the present invention. Media file 30 can be a compilation of one or more activity modules. Each module can store audio and/or visual information for one type of activity. When the user is compiling the program of activities stored in media file 30, the user may choose the modules the user wants to include in media file 30 and set global user-programmable parameters associated with media file 30. For example, a global user-programmable parameter can include the total amount of time a user has allocated to perform all the activities associated with media file 30. The user also may set module-specific user-programmable parameters associated with each module the user includes in the media file. For example, module 1 can be a fitness module instructing the user to lift weights using barbells. User-programmable parameters associated with module 1 can include the song a user wants to hear when exercising to this module, the number of pounds the user wants to lift per barbell, and the number of repetitions a user wants to perform.

When the user is ready to perform the activities associated with media file 30, the user can initiate playback of media file 30 on electronic device 10. Electronic device 10 then can begin playing module 1 by outputting the audio and/or visual information associated therewith. Upon the completion of module 1, the electronic device 10 can automatically begin playing module 2 by outputting the audio and/or visual information associated therewith. This process can continue until electronic device 10 has played all of the modules.

In accordance with one aspect of the present invention, controller 18 can be configured to permit a user to adjust global and/or module-specific user-programmable parameters of media file 30 during playback of the media file. Controller 18 can display one or more icons on display 14 that correspond to the user-programmable parameters of media file 30. Using user input component 16, the user may select the icon corresponding to the user-programmable parameter he wishes to modify. Once controller 18 has visually distinguished the selected icon, the user can modify the user-programmable parameter by manipulating user input component 16.

Figure 3A:
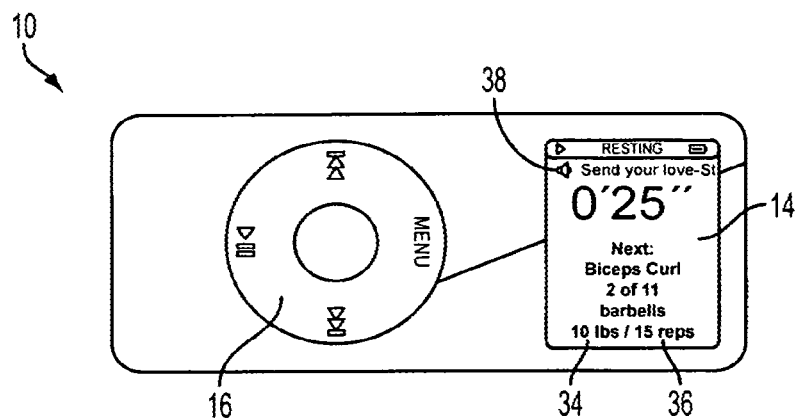
FIGS. 3A-3B illustrate an electronic device that permits a user to adjust user-programmable parameters of a media file during playback of the media file in accordance with one embodiment of the present invention.
Figure 3B:
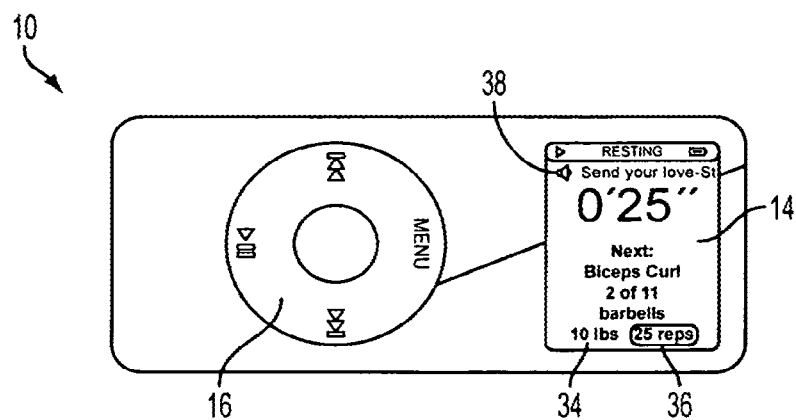

FIGS. 3A-3B illustrate an electronic device that permits a user to adjust user-programmable parameters of a media file during playback of the media file in accordance with one embodiment of the present invention. Controller 18 of electronic device 10 can display multiple icons 34-38 on display 14 of electronic device 10. Icons 34-36 can correspond to global and/or module-specific user-programmable parameters of media file 30. Icon 38 can correspond to media file-independent parameters of the electronic device associated with playback of the media file (e.g., volume and/or an equalizer). Controller 18 can permit a user to tab through icons 34-38 using user input component 16 until a desired icon is visually distinguished from the other icons (e.g., highlighted or bolded). Once the desired icon is selected, the controller may permit the user to modify parameters associated with the selected icon by manipulating user input 16.

In the illustrative embodiment shown in FIGS. 3A-3B, electronic device 10 may be playing a media file that walks a user through a fitness routine similar to that discussed in the incorporated patent documents. The user may have programmed the fitness routine with a fitness module that instructs the user to lift weights using barbells. As shown in FIG. 3A, the user may have initially programmed the module to instruct the user to perform 15 repetitions of bicep curls using 10 pound barbells. However, during the fitness routine, the user may decide he wants to increase the number of repetitions to 25. Electronic device 10 can permit a user to indicate this adjustment by toggling through icons 34-38 by manipulating user input 16 (e.g., the buttons of a clickwheel) until the user reaches desired icon 36. Icon 36 can correspond to the user-programmable parameter associated with the number of repetitions saved in the media file. As shown in FIG. 3B, once desired icon 36 is visually distinguished from the other icons (e.g., highlighted), electronic device 10 can permit the user to adjust the number of repetitions (e.g., from 15 to 25) by manipulating user input 16 (e.g., by scrolling through values using a clickwheel similar to that incorporated in the iPod™). Electronic device 10 then can display adjustments to the selected user-programmable parameter in the corresponding icon, as shown in FIG. 3B.

Figure 4A:
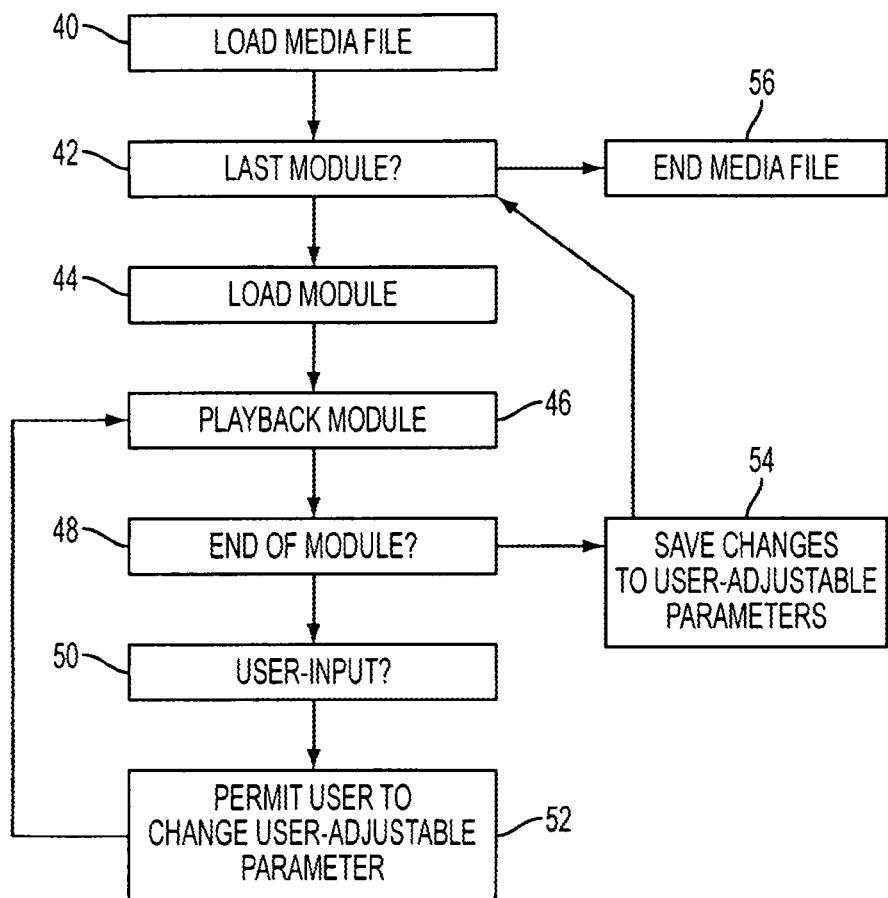
FIGS. 4A-4B illustrate a process for use by the electronic device of FIGS. 3A-3B in accordance with one embodiment of the present invention.
Figure 4B:
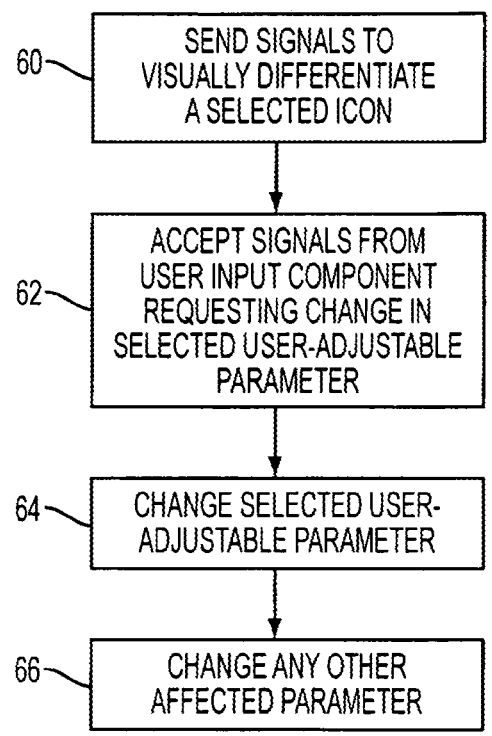

FIGS. 4A-4B illustrate a process for use by electronic device 10 of FIGS. 3A-3B in accordance with one embodiment of the present invention. In step 40, controller 18 of electronic device 10 can accept signals from user input component 16 to load a desired media file for playback. Once the media file is loaded, controller 18 can check to see whether the controller has played the last module of the media file in step 42. Since the controller has just loaded the user-selected media file, controller 18 can then progress onto step 44, in which it can load the first module in the media file.

In step 46, controller 18 can begin playing the first module of the media file. This can include outputting audio and/or visual information associated with that module, displaying icon(s) 38 on display 14 corresponding to media file-independent parameters, and logging information collected by sensors S. Visual information associated with a module can include icons 34-36 that identify user-programmable parameters that a user can adjust during playback of that module, the amount of time elapsed, visual cues for the proper way to perform the activity associated with the current module playing, visual cues of the activity associated with the next module to be played from the media file, etc.

In step 48, controller 18 can check whether the end of the module has been reached. If not, in step 50, controller 18 can wait to accept signals from user input component 16 that indicate the user wishes to adjust either a user-programmable parameter associated with the media file or a media file-independent parameter. Once the controller receives one or more signals from user input component 16, controller 18 can permit the user to adjust a user-programmable parameter or one of the media file-independent parameters in step 52. Thereafter, controller 18 can reiterate steps 46-52 to continue playing the first module of the loaded media file in accordance with the adjustment made to a user-programmable parameter in step 52.

Once controller 18 detects that it has reached the end of the first media module in step 48, controller 18 can save any adjustments made to user-programmable parameters associated with the first media module in step 54. Alternatively, the controller can save adjustments to the user-programmable parameters immediately after the adjustments are made.

Thereafter, controller 18 can automatically load and begin playback of a second media module of the loaded media file. Because the second module can request that the user perform an activity different than that of the first module, the controller may output different audio and/or visual information than that output for the first module and/or log different information collected by sensors S. Controller 18 can continuously reiterate steps 42-54 until the controller detects in step 42 that it has just played the last module of the loaded media file. In step 56, controller 18 can conclude playback of the media file loaded in step 40.

Once the user has completed the scheduled activities, the user can upload the adjustments made to the user-programmable parameters of the media file into local server 24 and/or central server 26 along with other data that electronic device 10 collected about the user's performance. Local server 24 and/or central server 26 then can analyze the uploaded data to adapt the user's goals or otherwise track a user's progress.

FIG. 4B illustrates a process for use by electronic device 10 in step 52 of FIG. 4A in accordance with one embodiment of the present invention. In response to receipt of signals from user input component 16 in step 50, controller 18 can send signals to display 14 to visually distinguish a selected icon 34-38 in step 60. In step 62, controller 18 can accept signals from user input component 16 that indicates the user is requesting to adjust the user-programmable parameter or media file-independent parameter corresponding to the selected icon. In step 64, controller 18 can adjust the selected user-programmable or media file-independent parameter.

Adjustments in global or module-specific user-programmable parameters during step 64 may require that controller 18 adjust the playback of the remainder of the media file. In step 66, controller 18 can make adjustments in other user-programmable and non-user-programmable parameters of the loaded media file in response to adjustments made in step 64. For example, if the user adjusts the number of repetitions from 15 to 25 as shown in FIGS. 3A-3B, controller 18 may need to allocate a greater amount of time for the user to perform and for the controller to play back the entire media file. Thus, controller 18 may need to make a corresponding adjustment to a global user-programmable parameter of the loaded media file, e.g., the total amount of time a user has allocated to perform all the activities of media file 30. Alternatively, rather than changing a global parameter of the media file, controller 18 can instead adjust a user-programmable parameter of a media module that is scheduled to be played after the current module. For example, the controller can instead shorten the time allocated for a user to perform another fitness module, e.g., a jogging module.

While the media file described above can store both audio and visual data, media files of the present invention also may be configured to store only audio data or only visual data. Furthermore, an electronic device of the present invention can permit a user to adjust user-programmable parameters associated with any type of file, not just a media file.

FIGS. 5A-5D illustrate an electronic device of the present invention that can automatically re-orient image I shown on its display based on the orientation of the device. For example, assume that electronic device 10 and image I are disposed in a reference orientation in FIG. 5A. When electronic device 10 is rotated from its reference orientation, controller 18 can detect the rotation based on signals from orientation transducer 22. Responsive thereto, controller 18 can rotate image I on display 14 so that it remains in the reference orientation (e.g., oriented upright in the positive Y direction). For example, when electronic device 10 is rotated by 90 degrees so that it is positioned parallel to the X axis (the orientation shown in FIGS. 5B or 5C), controller 18 can maintain image I on display 14 in the reference orientation. Similarly, when electronic device 10 is rotated by an additional 90 degrees as shown in FIG. 5D, controller 18 also can maintain image I on display 14 in the reference orientation.

Image I can include text images, still images, and/or video images. For example, image I can include icons 34-38 as discussed above with respect to FIGS. 1-4.

While FIGS. 5A-5D illustrate image I oriented in either a portrait or landscape orientation based on the orientation of electronic device 10, controller 18 also can be configured to orient image I in intermediate orientations.

Figure 5E:
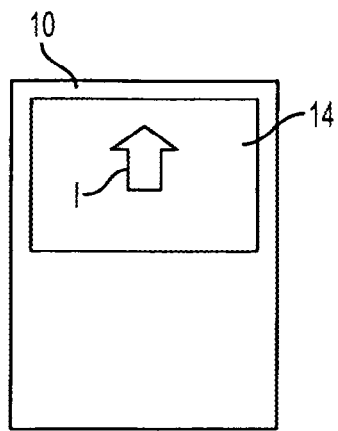
Figure 5F:
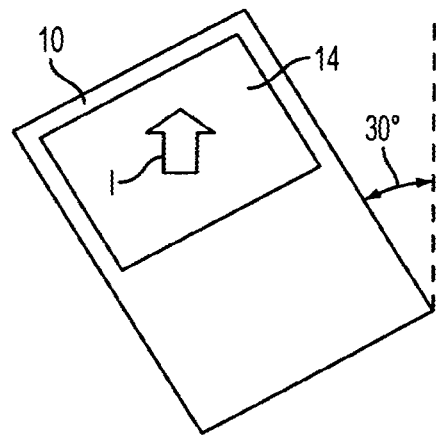
Figure 5G:
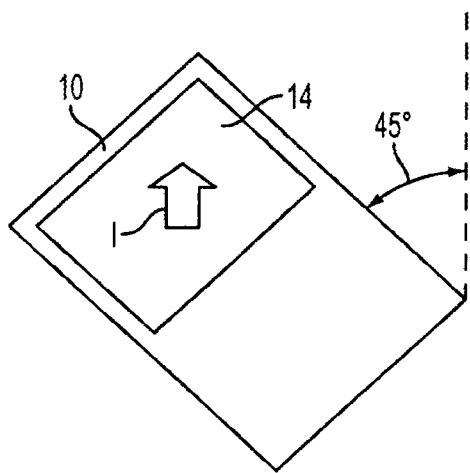
Figure 5H:
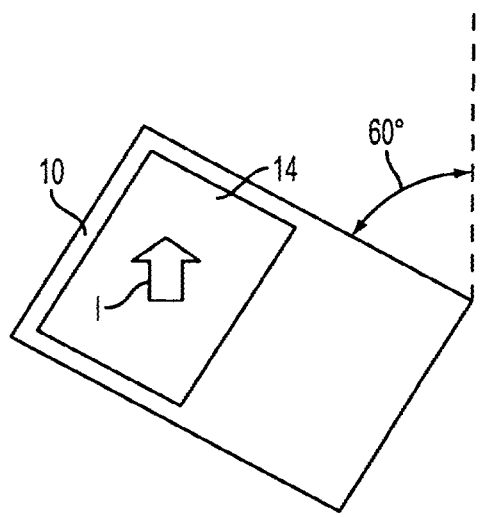
Figure 5I:
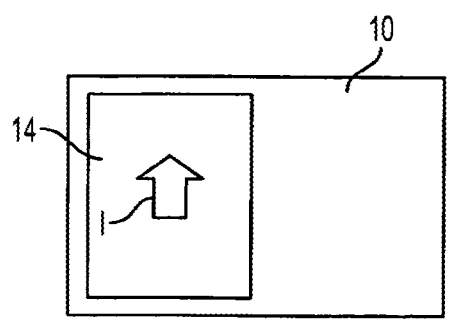

FIGS. 5E-5I illustrate an electronic device of the present invention that can re-orient image I in one of a plurality of orientations ranging from the portrait orientation of FIG. 5E to the landscape orientation of FIG. 5I, inclusive. Thus, as shown in FIGS. 5F-5H, the orientation of image I can be rotated by less than 90 degrees with respect to either the orientation of FIGS. 5E or 5I. In one embodiment of the present invention, each of the orientations shown in FIGS. 5E-5I can be a discrete orientation in which image I can be disposed. Alternatively, the orientations shown in FIGS. 5E-5I can represent a non-discrete set of orientations in which image I can be disposed. In the latter case, electronic device 10 can be configured to re-orient image I so that image I continuously tracks the orientation of electronic device 10. Thus, each successive re-orientation of image I can merge smoothly with the next so that changes in the orientation of image I are not disjointed.

Although FIGS. 5A-I illustrate different orientations of electronic device 10 in two dimensions, electronic device 10 also can be oriented in three-dimensions. Accordingly, controller 18 can be configured to re-orient image I based on the orientation of electronic device 10 in three-dimensions. For example, controller 18 can re-orient image I based on the orientation of device 10 in the X-, Y-, and Z-axes. When electronic device 10 is tilted out of the X-Y plane, controller 18 can detect the rotation based on signals from orientation transducer 22. Responsive thereto, controller 18 can re-orient image I so that it remains in a manufacturer or user-defined reference orientation.

Orientation transducers incorporated in the electronic devices of the present invention can include a single multi-dimensional motion sensor or an assembly of sensors that can detect motion of the electronic device, including position, orientation, and/or movement. For example, an orientation transducer can include one or more multi-dimensional accelerometers, GPS systems, gyroscopes, magnetic sensors, mercury switches, or any combination thereof. The orientation transducers also can include a receiver that can triangulate the position, orientation, and/or movement of the electronic device based on signals received from multiple transmitters disposed near the receiver.

Advantageously, an electronic device that can dynamically adjust the orientation of image I in the manner described may be useful for a user who may position the electronic device in a non-standard orientation. For example, an athlete may have an iPod™ strapped to his forearm. When the athlete has his arm extended in front of him (e.g., when he is stretching before a jog), he may wish to view image I on a display of the iPod™ in the orientation shown in FIG. 5A. However, when the athlete's forearm is positioned close to his chest (for example, when the athlete wants to check the elapsed time or the song that is currently playing on his iPod™), it may be more convenient for the athlete to view image I in the orientation of FIGS. 5B or 5D. Electronic device 10 may re-orient image I on its display as the athlete moves his forearm closer to his chest.

Figure 6A:
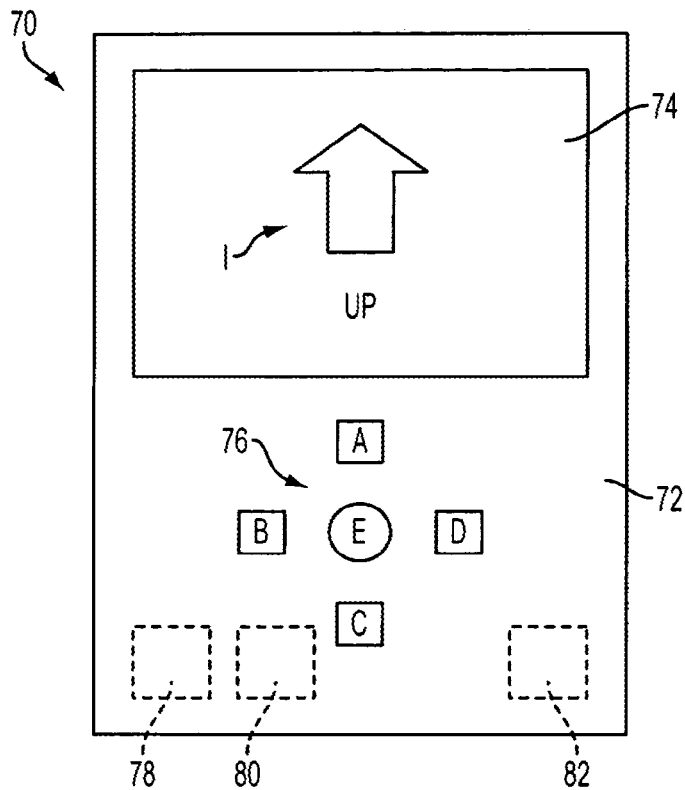
FIGS. 6A-6B illustrate an electronic device that can automatically re-orient an image shown on its display and re-configure user input components based on the orientation of the device in accordance with one embodiment of the present invention.
Figure 6B:
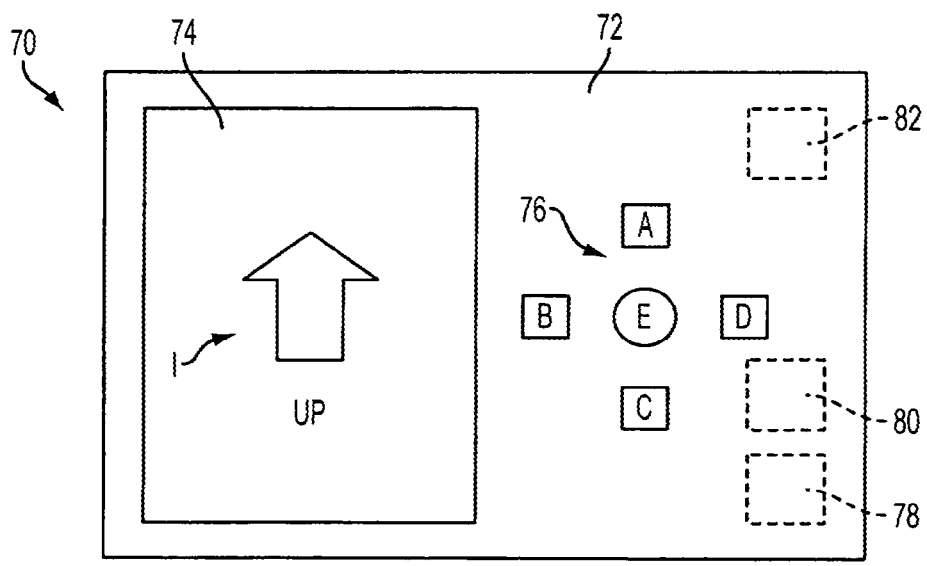

FIGS. 6A-6B illustrate one embodiment of an electronic device that can automatically re-configure a hardware user input component based on the orientation of the device. Electronic device 70 can include housing 72, display 74, hardware user input component 76, controller 78, memory 80, and orientation transducer 82. Hardware user input component 76 can include, e.g., multiple buttons associated with functions A-E.

When electronic device 70 is oriented in a reference orientation (e.g., the positive Y direction shown in FIG. 6A), buttons associated with functions A-E also can be configured in a reference orientation (e.g., with the button associated with function A disposed closest to display 74). When electronic device 70 rotates from its reference orientation (e.g., into the orientation shown in FIG. 6B), controller 78 can detect the rotation based on signals from orientation transducer 82. Responsive thereto, controller 78 can re-configure user input component 76 so that the user does not perceive a change in the configuration of the user input component despite re-orientation of electronic device 70. For example, controller 78 can re-configure user input component 76 by re-assigning functions A-D so that function A always is assigned to the button disposed in the positive Y direction relative to the button assigned with function E, function B always is assigned to the button disposed in the negative X direction relative to the button assigned with function E, function C always is assigned to the button disposed in the negative Y direction relative to the button assigned with function E, and function D always is assigned to the button disposed in the positive X direction relative to the button assigned with function E.

Controller 78 can re-configure the buttons of user input 76 when electronic device 70 is re-oriented by, e.g., using one or more hardware switches or multiplexers. Alternatively, controller 78 can incorporate software that distributes signals received from the buttons of user input 76 to the appropriate function based on signals from orientation transducer 82.

Figure 6C:
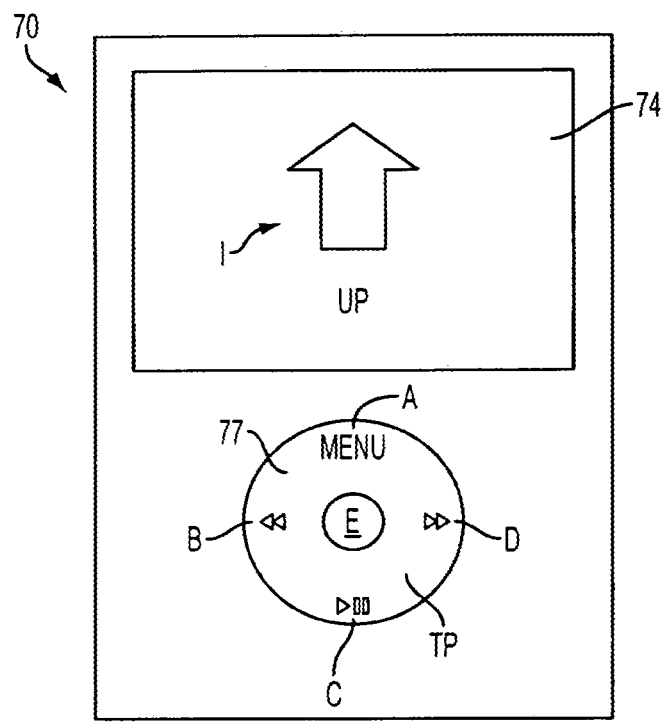
FIGS. 6C-6D illustrate an electronic device that can automatically re-orient an image shown on its display based on the orientation of the device and permit a user to manually re-configure a user input component in accordance with one embodiment of the present invention.
Figure 6D:
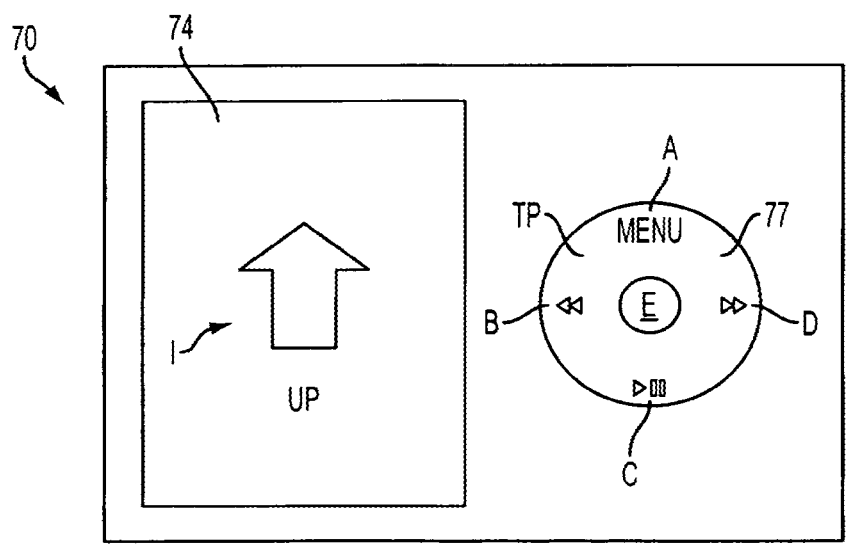

FIGS. 6C-6D illustrate electronic device 70 with an alternative user input component that can be re-configured with re-orientation of the device. User input component 77 can be similar to the clickwheel incorporated in some models of iPods™. User input component 77 can incorporate touchpad TP and a plurality of buttons assigned with functions A-E. In one embodiment of the present invention, user input component 77 can be manually re-configured by a user when the user changes the orientation of device 70. For example, user input component 77 can be configured to be manually rotated clockwise or counterclockwise. Thus, when a user re-orients electronic device 70 from the orientation of FIG. 6C to that of FIG. 6D, the user also can rotate user input component 77 by 90 degrees to dispose the user input component in a more ergonomic configuration.

Electronic device 70 also can provide tactile feedback to the user during manual re-configuration. For example, there can be mechanical stops that prevent the user from rotating user input 77 past certain angles. Also, user input component 77 can incorporate mechanical protuberances that are configured to engage depressions (or vice versa). When the user manually re-configures user input component 77, electronic device 70 can provide tactile feedback to the user when the protuberances engage the depressions.

FIGS. 7A-7E illustrate an electronic device that can automatically re-configure user input components based on the orientation of the device. Electronic device 90 can include housing 92, display 94, and controller 98. Controller 98 can overlay icons 104 onto image I shown on display 94 or incorporate icons 104 into image I. Icons 104 can be disposed on display 94 in locations on or proximate to software or hardware user input components. The icons can have shapes, text or images that indicate the functions of the input components designated by the icons. For example, if display 94 is a touchscreen display, icons 104 can indicate the locations of software input components, e.g., software buttons assigned with functions A-F (see FIG. 7A-7C). A user then may actuate any of the software buttons by contacting or otherwise interacting with display 94 at the locations at which icons 104 are disposed. In addition to buttons, software user input components also can include linear or circular scrolls, sliders, dials, any other user interfaces that can be emulated on display 94, or any combination thereof. Touchscreen displays can include any touch or proximity sensitive display known in the art or otherwise that can simultaneously (1) display image I and icons 104, and (2) detect when a user wants to actuate a software user input component.

Figure 7A:
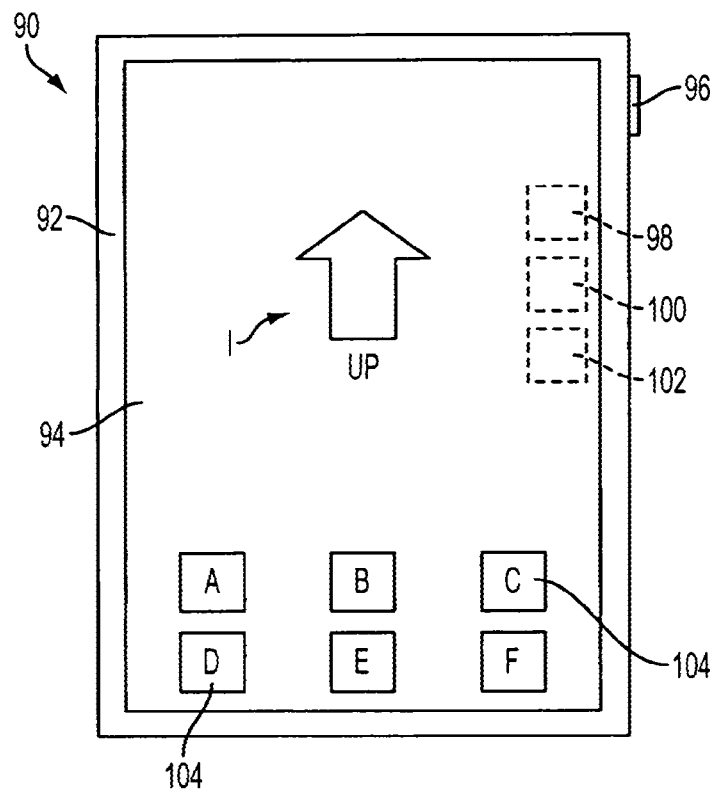
FIGS. 7A-7E illustrate electronic devices that can automatically re-orient an image shown on its display and re-configure user input components based on the orientation of the device in accordance with one embodiment of the present invention.
Figure 7B:
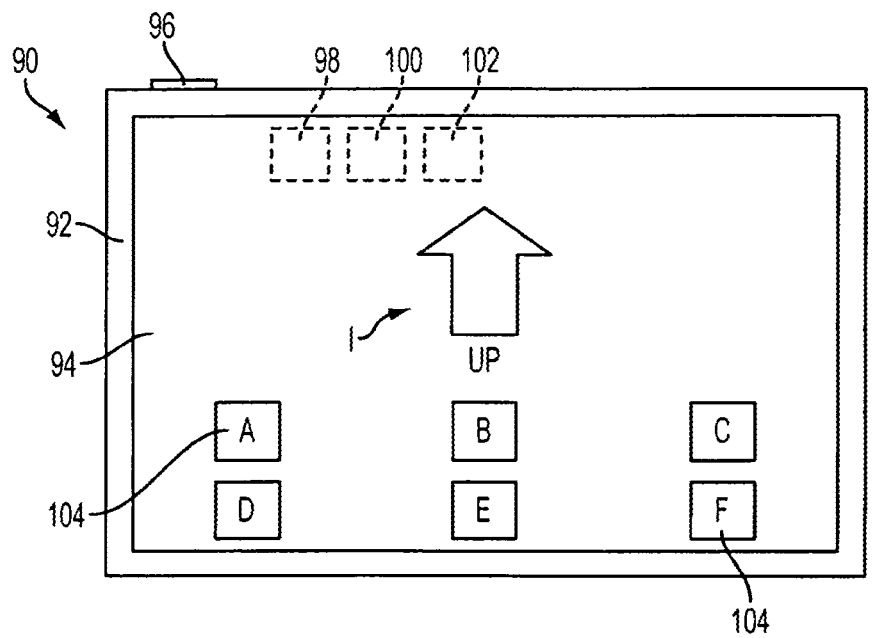
Figure 7C:
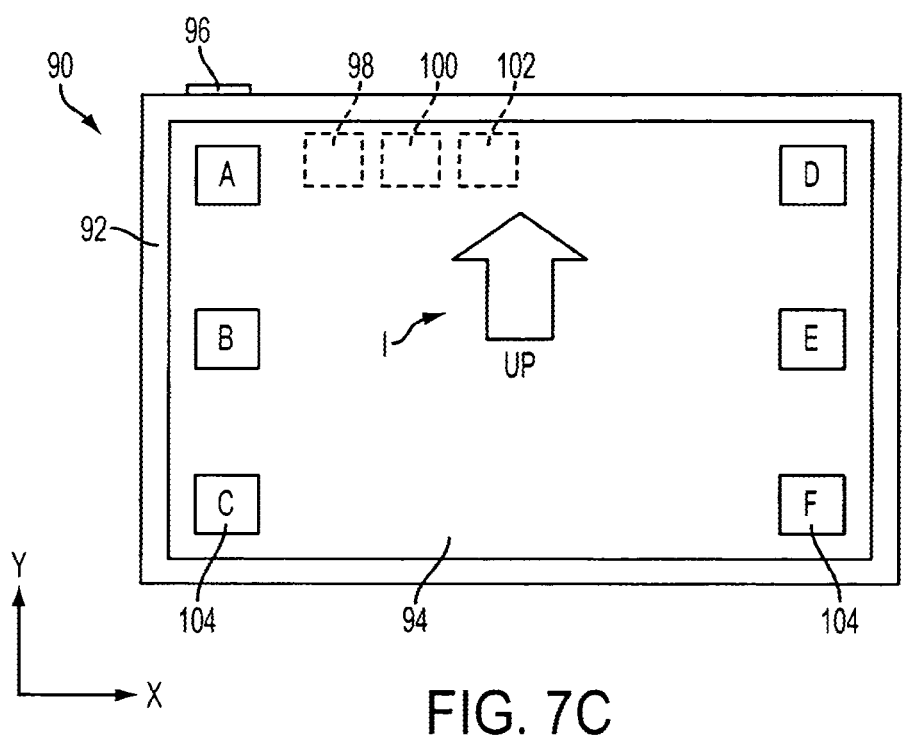
Figure 7D:
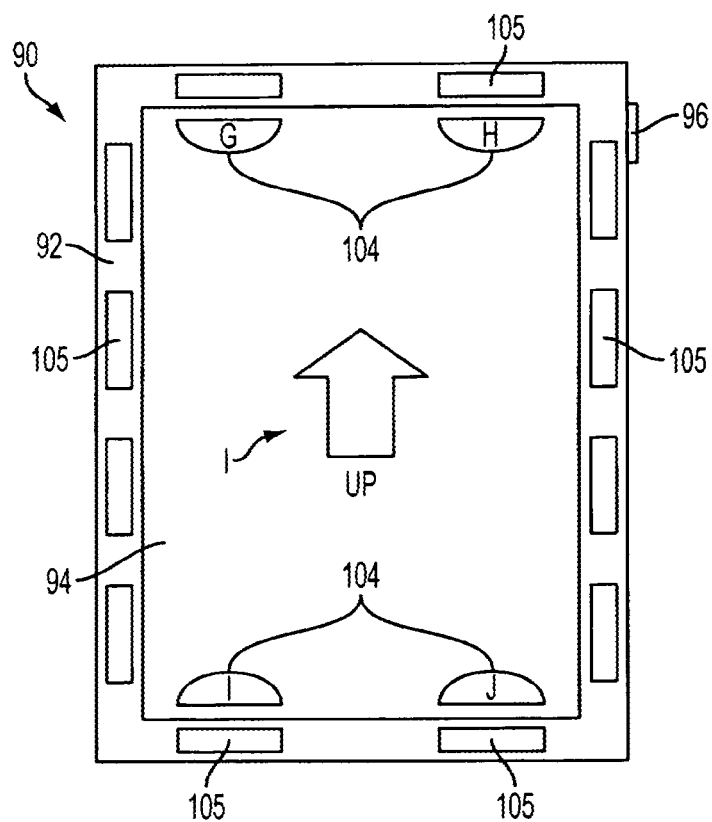
Figure 7E:
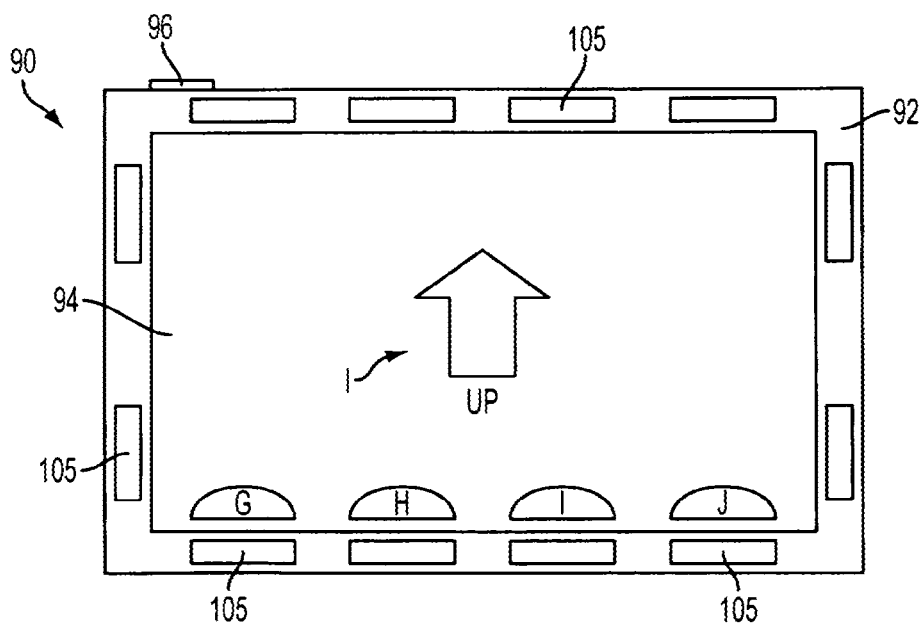

As illustrated in FIGS. 7D-7E, icons 104 also can be disposed proximate to hardware input components 105. Hardware input components 105 can include hardware buttons assigned with functions G-J, linear or circular scroll, slider, dial, one of the user input components described in the incorporated King document, any other type of hardware that can be used for user input, or any combination thereof.

As shown in FIGS. 7A and 7D, controller 98 can display image I and icons 104 on display 94 in a reference orientation. When electronic device 90 changes orientation, e.g., rotates counter-clockwise by 90 degrees as shown in FIGS. 7B, 7C, and 7E, controller 98 can detect the rotation based on signals from orientation transducer 102. Responsive thereto, controller 98 can re-orient image I and re-configure the user input components designated by icons 104.

For example, as illustrated in FIG. 7B, controller 98 can re-position the software input components and icons 104 so that the composite image formed by image I and icons 104 stays the same with the re-configuration. Alternatively, as illustrated in FIGS. 7C, controller 98 can re-position the software input components and icons 104 so that the composite image formed by image I and icons 104 change as a result of the re-configuration. In the embodiment of FIGS. 7E, controller 98 can re-assign functions to one or more of components 105 and re-position icons 104. Again, functions G-J can be re-assigned so that the composite image formed by image I and icons 104 change as a result of the re-configuration. An electronic device of the present invention may change the composite image formed by image I and icons 104, for example, to better distribute icons 104 within a display (as shown in FIG. 7C) and/or when all active user input components are consolidated along a single side of the display that is more accessible to a user (as shown in FIG. 7E).

Electronic device 90 also can include hardware user input component 96, memory 100, and orientation transducer 102. Memory 100 can store, for example, media files with which image I is associated, data from which controller 98 can generate icons 104, and program code. The program code can include, for example, instructions for displaying, re-orienting, and re-configuring image I, icons 104, software input components, and hardware input components 105. Hardware user input component 96 can be, for example, a single or multi-functional button. Multi-functions buttons can signal controller 98 to perform one function when a user depresses the button for a predetermined amount of time and signal controller 98 to perform a second function when a user depresses the button for a shorter amount of time.

Figure 8:
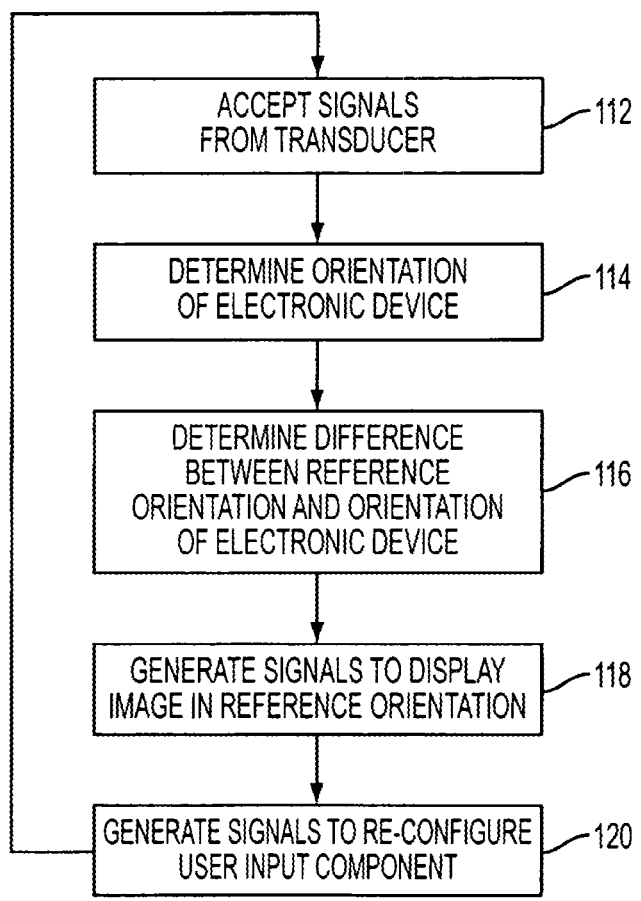
FIG. 8 illustrates a process for use by an electronic device of one embodiment of the present invention to re-orient an image shown on a display and re-configure a user input component based on the orientation of the device.

FIG. 8 illustrates one embodiment of a process for use by an electronic device of the present invention to re-orient an image on a display and re-configure one or more user input components of the device based on the orientation of the electronic device. In step 112, a controller can accept signals from an orientation transducer disposed within the electronic device. In step 114, the controller can analyze the signals from the orientation transducer to determine the orientation of the electronic device. In step 116, the controller can determine the difference between the orientation of the electronic device and a reference orientation.

The controller may permit a manufacturer or a user to set the reference orientation. For example, a user may set the reference orientation of the electronic component in the positive X direction, rather than, e.g., the positive Y direction shown in FIG. 5A. Thereafter, the controller can maintain images displayed by the device oriented in the positive X direction regardless of the orientation in which the electronic device is disposed.

In step 118, the controller can generate signals to re-orient an image in the reference orientation. Depending on the determination made in step 116, this can include rotating the image into the reference orientation and performing any other operations necessary to properly display the image in the new orientation, e.g., scaling.

To rotate the image, the controller can use transformation matrices or select from versions of the image stored in memory that already are disposed in predetermined orientations. For example, each time the controller determines that the reference orientation is different than the real-time orientation of the electronic device, the controller can determine a transformation matrix based on the reference orientation and the real-time orientation of the electronic device. The transformation matrix also can incorporate factors needed to properly display the image in the new orientation (e.g., scaling factors). The controller then can use the transformation matrix to re-orient the image. Advantageously, this technique may be useful for re-orienting images that are constantly changing, e.g., video images.

The electronic device also can store multiple versions of each image disposed in multiple orientations. The controller then can select and display the version of the image having the appropriate orientation based on the determination made in step 116. This may be useful for re-orienting still images that are repeatedly displayed in certain predetermined orientations.

Alternatively, rather than storing multiple versions of each image, the electronic device can store predetermined transformation matrices that can re-orient any image to be displayed by the electronic device. Again, the controller can incorporate, e.g., scaling factors into the stored transformation matrices. The controller then can select the appropriate transformation matrix based on the determination made in step 116 and apply the transformation matrix to re-orient the image. Again, this technique may be useful for re-orienting images that are constantly changing.

The controller also can use other techniques known in the art or otherwise to re-orient an image shown on a display of the electronic device.

In step 120, the controller can generate signals to re-configure one or more user input components of the electronic device. This can include re-assigning functions to one or more user input components, re-positioning one or more user input components, and/or re-positioning one or more icons that designate user input component(s).

In accordance with another aspect of the present invention, a controller can permit the user to reversibly deactivate certain orientations in which the controller is capable of displaying an image. For example, the controller can permit a user to limit an image to be displayed only in the following two orientations: the orientation of FIG. 5A or the orientation of FIG. 5B. The controller also may permit the user to reversibly deactivate the automatic re-orientation feature of the electronic device. Instead, the controller can require that the user toggle images on the display among different orientations by manually signaling the controller using a user input component.

Similarly, the controller can permit the user to reversibly deactivate certain configurations in which the controller is capable of re-configuring user input components. The controller also can permit the user to reversibly deactivate the automatic re-configuration feature of the electronic device. Again, the controller can instead require that the user toggle between configurations of the user input component by manually signaling the controller.

Although particular embodiments of the present invention have been described above in detail, it will be understood that this description is merely for purposes of illustration. Alternative embodiments of those described hereinabove also are within the scope of the present invention.

Electronic devices of the present invention can combine features described above with respect to FIGS. 1-8. For example, an electronic device of the present invention can permit a user to change user-programmable parameters of a media file, automatically re-orient images based on the orientation of the electronic device, and automatically re-configure user input components based on the orientation of the electronic device.

Electronic devices of the present invention also can include other components that are not illustrated in FIGS. 1-8 for the sake of simplicity, e.g., a receiver to receive data from sensors S, additional input components, and/or additional output components.

Electronic devices of the present invention can be any electronic device that executes files having user-programmable parameters and/or any electronic device that a user may orient in a non-standard orientation. For example, the electronic device can be any portable, mobile, hand-held, or miniature consumer electronic device. Illustrative electronic devices can include, but are not limited to, music players, video players, still image players, game players, other media players, music recorders, video recorders, cameras, other media recorders, radios, medical equipment, calculators, cellular phones, other wireless communication devices, personal digital assistances, programmable remote controls, pagers, laptop computers, printers, or any combination thereof. Miniature electronic devices may have a form factor that is smaller than that of hand-held devices. Illustrative miniature electronic devices can include, but are not limited to, watches, rings, necklaces, belts, accessories for belts, headsets, accessories for shoes, virtual reality devices, other wearable electronics, accessories for sporting equipment, accessories for fitness equipment, key chains, or any combination thereof.

The above described embodiments of the present invention are presented for purposes of illustration and not of limitation, and the present invention is limited only by the claims which follow.

What is claimed is:

1. A system comprising:
   an output component;
   an input component;
   a memory component; and
   a processor that:
     plays back a media file from the memory component for providing media information to a user about a plurality of activities of the media file via the output component;
     receives a user input command from the input component during the playback of the media file; and
     based on the received user input command, adjusts a programmable parameter of the media file during the playback of the media file, wherein:
       the parameter adjustment adjusts the media file;
       the media file adjustment adjusts the playback of the remainder of the media file after the parameter adjustment;
       the playback adjustment affects the media information provided to the user during the playback of the remainder of the media file after the parameter adjustment;
       the processor plays back the media file by:
         playing back a first media module of the media file that provides first media information about a first activity of the plurality of activities; and
         after playing back the first media module, playing back a second media module of the media file that provides second media information about a second activity of the plurality of activities;
       the processor receives the user input command during the playback of the first media module; and
       the parameter adjustment affects the playback of the second media module.

2. The system of claim 1, wherein the input component, memory component, and processor are provided by a portable electronic device.

3. The system of claim 1, wherein the parameter adjustment is stored in the memory component.

4. The system of claim 1, wherein the parameter comprises a global parameter associated with a total time allocated to perform every activity of the plurality of activities of the media file.

5. The system of claim 1, wherein the parameter is associated with a total time allocated to perform both the first activity and the second activity.

6. A system comprising:
   an output component;

an input component;
a memory component; and
a processor that:
   plays back a media file from the memory component for providing media information to a user via the output component;
   receives a user input command from the input component during the playback of the media file; and
   based on the received user input command, adjusts a programmable parameter of the media file during the playback of the media file, wherein:
      the parameter adjustment adjusts the media file;
      the media file adjustment affects the media information provided to the user during the playback of the remainder of the media file after the media file adjustment;
      the processor plays back the media file by:
         playing back a first media module of the media file that provides first media information; and
         after playing back the first media module, playing back a second media module of the media file that provides second media information;
      the processor receives the user input command during the playback of the first media module;
      the parameter comprises a first parameter that is associated with the first media module; and
      based on the adjustment to the first parameter, the processor adjusts a second parameter of the media file during playback of the media file.

7. The system of claim 6, wherein the second parameter comprises a global parameter of the media file.

8. The system of claim 6, wherein the second parameter comprises a module-specific parameter.

9. The system of claim 8, wherein the second parameter is associated with the first media module.

10. The system of claim 8, wherein the second parameter is associated with the second media module.

11. A method comprising:
   playing back a media file for providing media information to a user;
   receiving an input command during the playing back of the media file; and
   based on the received input command, adjusting a programmable parameter of the media file during the playing back of the media file, wherein:
      the adjusting the programmable parameter comprises adjusting the media file;
      the adjusting the media file affects the media information provided to the user during the playing back of the remainder of the media file after the adjusting the media file;
      the playing back comprises:
         playing back a first media module of the media file that provides first media information; and
         after the playing back of the first media module, playing back a second media module of the media file that provides second media information;
      the receiving the input command occurs during the playing back of the first media module; and
      the adjusting the media file affects the playing back of the second media module.

12. The method of claim 11, wherein the playing back, the receiving the input command, and the adjusting the parameter are accomplished by a portable electronic device.

13. The method of claim 11, further comprising storing the parameter adjustment in a memory component.

14. The method of claim 11, wherein:
   the playing back the first media module of the media file provides first media information about a first activity; and
   the playing back the second media module of the media file provides second media information about a second activity; and
   the programmable parameter is associated with a total time allocated for the user to perform both the first activity and the second activity.

15. The method of claim 11, wherein the programmable parameter comprises a first parameter that is associated with the first media module.

16. The method of claim 11, wherein:
   the programmable parameter comprises a first parameter that is associated with the first media module; and
   based on the adjusting the first parameter, the method further comprises adjusting a second parameter of the media file during the playing back of the media file.

17. The method of claim 16, wherein the second parameter comprises a global parameter of the media file.

18. The method of claim 16, wherein the second parameter comprises a module-specific parameter.

19. The method of claim 18, wherein the second parameter is associated with the first media module.

20. The method of claim 18, wherein the second parameter is associated with the second media module.

* * * * *